United States Patent [19]

Gilby

[11] 4,175,864

[45] Nov. 27, 1979

[54] ASTIGMATIC ILLUMINATING SYSTEM IN AN INTERNAL REFLECTION SPECTOMETER

[75] Inventor: Anthony C. Gilby, Darien, Conn.

[73] Assignee: The Foxboro Company, Foxboro, Mass.

[21] Appl. No.: 879,197

[22] Filed: Feb. 21, 1978

[51] Int. Cl.² .............................................. G01J 3/42
[52] U.S. Cl. .................... 356/326; 356/244; 356/440
[58] Field of Search .................... 356/74, 94, 96, 97, 356/201, 244, 300, 319, 326, 244, 440

[56] References Cited

U.S. PATENT DOCUMENTS

| | | | |
|---|---|---|---|
| 3,022,704 | 2/1962 | Cary | 356/94 |
| 3,157,788 | 11/1964 | Roche | 356/74 UX |
| 3,582,209 | 6/1971 | La Rosa | 356/74 X |
| 3,606,547 | 9/1971 | Iwahasi | 356/97 |
| 3,927,944 | 12/1975 | Iwahashi et al. | 356/97 |

Primary Examiner—F. L. Evans
Attorney, Agent, or Firm—Garold E. Bramblett, Jr.

[57] ABSTRACT

In a spectrometer, an internal reflectance crystal having opposed internally reflecting surfaces extending between light-entrance and light-exit end surfaces is illuminated by a light source through a slit. The beam of light from the slit is reflected from a spherical mirror illuminated off-axis to form first and second astigmatic images of the slit. The tangential image, having a distorted (elongated or extended) height, is formed at the entrance surface of the internal reflectance crystal. The width of the tangential image matches the width of the entrance surface. The sagittal image is formed at the exit surface of the internal reflectance crystal. The width of the sagittal image, which would be distorted (extended) absent the internal reflectance crystal, is limited by the internally reflecting surfaces of the crystal. Thus, there is substantially no loss of radiant energy through the length of the crystal. In one embodiment, the exit surface is curved along its height to make the diverging beam leaving the internal reflectance crystal less divergent and thus more compact at the light detector lens.

19 Claims, 10 Drawing Figures

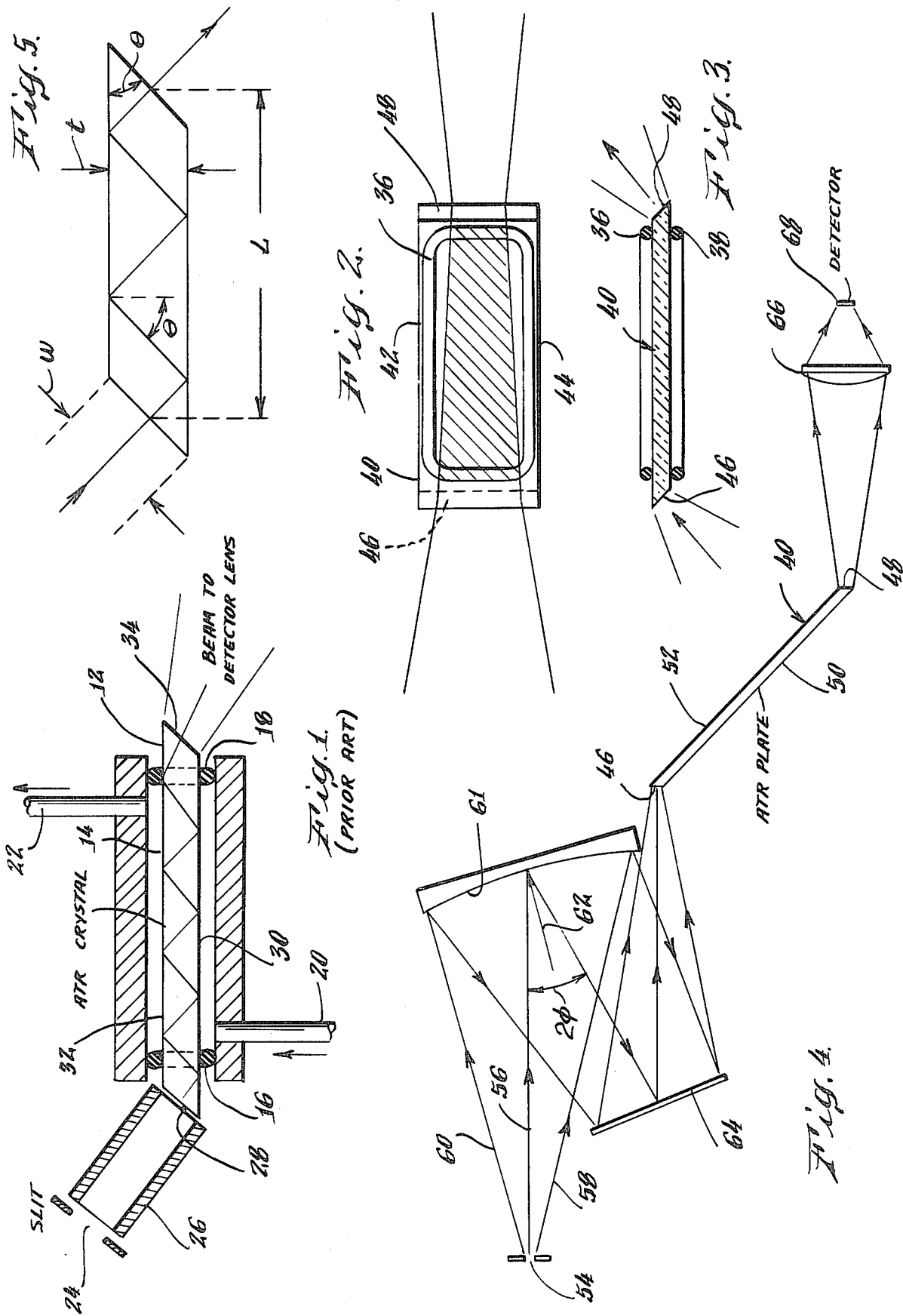

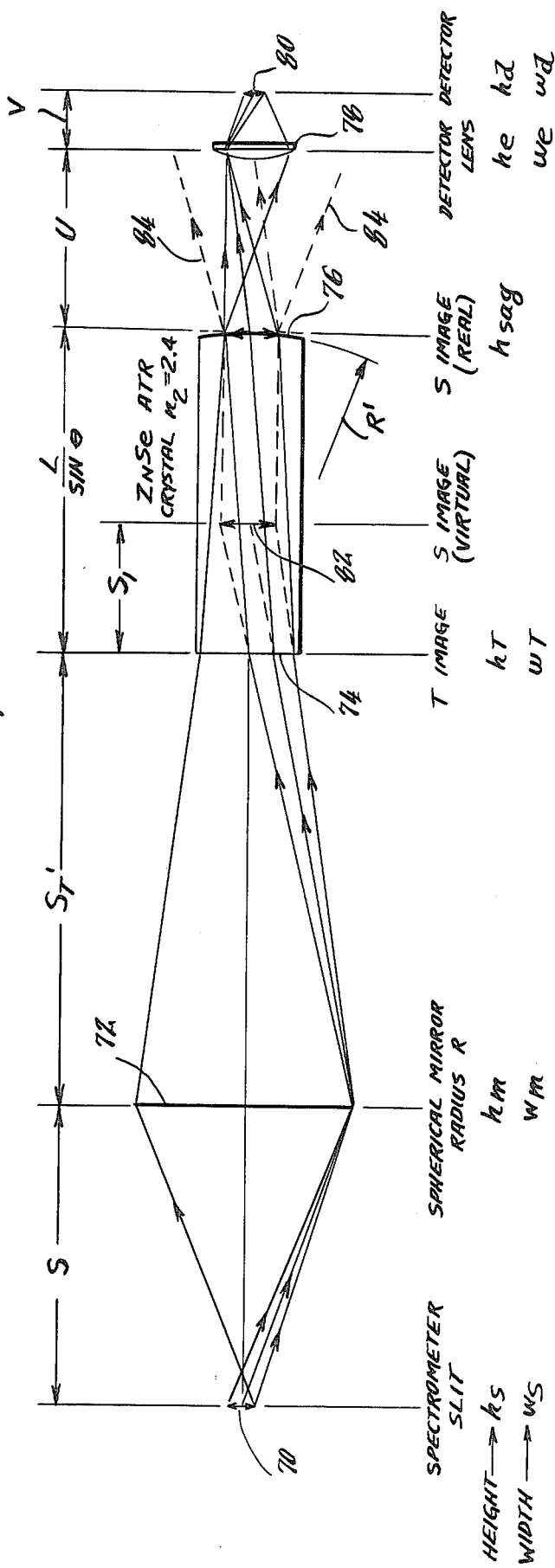

Fig. 8A — ILLUMINATION OF ENTRANCE SURFACE
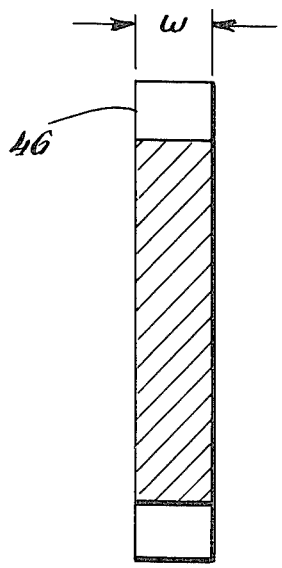
Fig. 8B — ILLUMINATION OF EXIT SURFACE
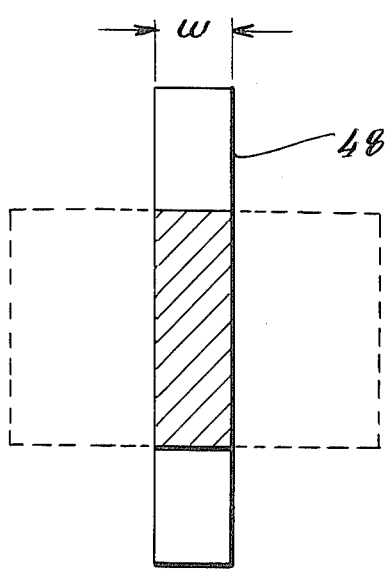
Fig. 9.
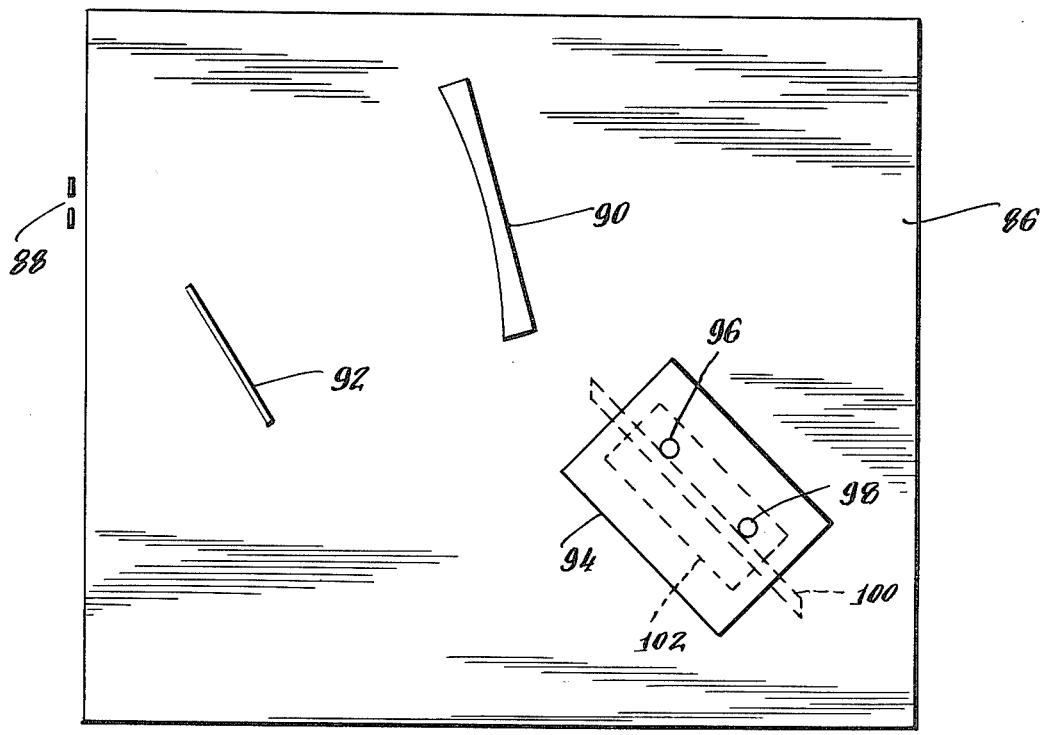

ASTIGMATIC ILLUMINATING SYSTEM IN AN INTERNAL REFLECTION SPECTROMETER

BACKGROUND OF THE INVENTION

This invention relates to spectrometers of the internal reflection type and, more particularly, to multiple internal reflection spectrometers utilizing crystals having opposed internally reflecting surfaces.

Multiple internal reflection spectrometry, also known as frustrated multiple internal reflection spectrometry or attenuated total reflection spectrometry (ATR), is based on the phenomenon that a light wave reflected from a totally internally reflecting interface is attenuated by a sample positioned beyond the interface. The light, which may include radiation within the ultraviolet, visible, or infrared ranges is attenuated at wavelengths specific to the sample.

One prior internal reflection apparatus is shown in FIG. 1. An ATR crystal 12 having a rectangular cross section is positioned in a sample chamber 14 by O-ring seals 16 and 18. A sample fluid enters the sample chamber 14 through an inlet tube 20 and leaves the chamber through an outlet tube 22. The internal reflectance crystal is illuminated by a light source through a slit 24. The slit width matches the width of the ATR crystal end face 28 and, ideally, the end face 28 is placed adjacent the slit. However, due to physical restraints of the spectrometer design, a light pipe 26 is provided to direct the beam of light through the entrance end surface 28 of the internal reflectance crystal. The beam strikes the entrance surface substantially perpendicularly; thus the beam is transmitted into the crystal. The beam of light then strikes the internally reflecting surface 30 at an angle of incidence greater than the critical angle and is reflected to the opposed surface 32. The angle of incidence of the light beam striking the surface 32 is also greater than the critical angle. Thus, the light is reflected back and forth between the opposed internally reflecting surfaces 30 and 32 toward an exit end surface 34 bevelled with respect to the reflecting surfaces. The beam of light strikes the end surface 34 substantially perpendicularly and thus passes on to a detector (not shown). The frequency spectrum of the detected light beam identifies the sample adjacent the totally internally reflecting interfaces and allows its concentration to be determined.

The spectrometer shown in FIG. 1 presents several practical problems. For one, a tight seal is difficult with an O-ring surrounding a crystal of rectangular cross section. The right angles of the crystal tend to break the seal. This problem can be minimized by rounding the edges of the crystal or by use of seals as shown in FIGS. 2 and 3. O-rings 36 and 38 are positioned flush against the opposed internally reflecting surfaces of an ATR crystal 40 to define two separate sample chambers.

The utility of spectrometers using internal reflection sampling has been limited by the severe energy losses associated with the ATR crystal. In prior configurations an image of the spectrometer slit is formed on the entrance face of the ATR crystal, filling its width, and the beam diverges inside the crystal so that either the top and bottom edge surfaces 42 and 44 are contacted by the beam or the emerging beam is considerably higher than the entering one. Both situations lead to energy loss. This is particularly true for filter spectrometers with "fast" optical systems. For example, the beam emerging from the slit of one filter spectrometer is a rapidly divergent beam, about F/1.5. There are further energy losses due to light striking the O-ring seals, particularly where the seals are as shown in FIGS. 2 and 3.

The sealing of FIGS. 2 and 3 is used successfully with ATR systems having a less divergent beam, such as about F/6, passed through the center portion of a tall ATR crystal, for example, a crystal 20 millimeters (mm) high. With such systems, the beam of light does not diverge rapidly enough to completely fill the crystal; thus losses at the upper and lower edges and at the O-ring seals are avoided. However, the tall exiting image has a low energy density and cannot be efficiently directed to the detector. And a large aperture at the light source is often vital in providing a high signal to noise ratio. Hence, the less divergent beam is not always feasible.

An object of this invention is to provide an illuminating system in an internal reflection spectrometer which permits the use of a wide aperture light source and a large number of internal reflections while avoiding the losses which generally result from reflections from the upper and lower crystal edge surfaces and from O-rings flush against the internally reflecting surfaces, or from an oversize exit beam which cannot be efficiently transferred to a small detector.

SUMMARY OF THE INVENTION

In accordance with the invention in one of its aspects, an internal reflectance crystal is illuminated by an optical system including an image forming means for forming first and second astigmatic images of a light source, the first astigmatic image having a distorted height and the second astigmatic image having a distorted width.

According to a further aspect of the invention, the astigmatic image having a distorted height is formed at the entrance end surface of the internal reflector crystal and the second astigmatic image having the distorted width is formed at the exit end surface of the internal reflector crystal, such that there is substantially no loss of energy through the length of the crystal. According to a preferred embodiment of the invention, the astigmatic image forming means includes a spherical mirror illuminated off-axis.

According to a further embodiment of the invention, the exit end surface of the internal reflectance crystal is curved throughout its height to refract the beam of light as it passes through the exit end surface and thereby reduce the divergence of the beam directed toward the detector.

BRIEF DESCRIPTION OF THE DRAWINGS

The foregoing and other objects, features and advantages of the invention will be apparent from the following more particular description of the preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a top view of a flow-through multiple internal reflection apparatus as known in the prior art;

FIG. 2 is a side view of an internal reflectance crystal having O-ring seals flush against each internally reflecting surface and illustrating the pattern of light in a vertical plane in a crystal illuminated in accordance with the invention;

FIG. 3 is a top view, with the O-rings in section, of the reflectance crystal and seals of FIG. 2, illustrating the pattern of light in a horizontal plane;

FIG. 4 is a top view of a spectrophotometer system in accordance with the present invention, including a spherical mirror illuminated off-axis to form astigmatic images;

FIG. 5 is a side view of an internal reflectance crystal with dimensional designations;

FIG. 6 is an optical schematic of the illuminating beam in the system of FIG. 4 in a vertical plane along the optical axis;

FIG. 7 is an optical schematic of the illuminating beam in the system of FIG. 4 in a horizontal plane along the optical axis;

FIGS. 8A and 8B are respective views of the entrance and exit end surface of the crystal of FIGS. 2 and 3 illustrating the illumination of the end surfaces; and FIG. 9 is a top plan view of an accessory for practicing the invention with conventional spectrophotometers.

DESCRIPTION OF PREFERRED EMBODIMENTS

In FIG. 4, an internal reflectance crystal 40 has a light entrance end surface 46 and a light exit end surface 48 positioned in the optical path of a beam of light. Two opposed internally reflecting surfaces 50 and 52 extend between the end surfaces and are positioned to internally reflect the beam of light. Although not shown in FIG. 4, a test sample may be positioned adjacent at least one of the internally reflecting surfaces.

The ATR crystal 40 is illuminated by a light source through a slit 54. The beam of light emitted through the slit is projected along an optical axis 56 and has a solid angle defined by outer rays 58 and 60. The beam of light is reflected by a spherical mirror 61 illuminated off-axis relative to a radius 62. The optical axis 56 and radius 62 form an angle $\phi$. The converging beam reflected from the spherical mirror is directed toward a planar reflector 64 from which it is directed toward the ATR crystal 40.

A spherical mirror illuminated off-axis as shown focuses a beam of light with an astigmatism to form a first astigmatic image in the horizontal or tangential plane and a second astigmatic image in the vertical or sagittal plane. The tangential image is distorted in height and the sagittal image is distorted in width. The ATR crystal 40 is precisely positioned to receive the beam of light from the spherical mirror such that the tangential image is formed at about its entrance end surface and the sagittal image is formed at about its exit end surface. The diverging beam of light emitted from the exit end surface 48 is directed toward a detector lens 66 which focuses the beam onto a detector 68.

The optical illuminating system of FIG. 4 can best be understood with reference to the schematics of FIGS. 6 and 7 which show selected rays relative to the optical axis 56 in the sagittal and tangential planes respectively. Along the axis 56, the light passes through the slit at position 70 and diverges toward the spherical mirror at position 72. The light then converges toward the front face of the ATR crystal positioned at 74 and passes through the crystal to the exit end surface at position 76. From the exit end surface of the plate at position 76, the beam of light is directed toward the detector lens at position 78 and the detector 80.

Along the optical axis, the crystal has an effective length of $L/\sin \theta$, where L is the actual length of the ATR crystal as shown in FIG. 5, and $\theta$ is the angle of incidence of the beam of light relative to the internally reflecting surfaces of the crystal. As shown in FIG. 7, the effective width of the crystal is $w = t/\sin \theta$, where t is the actual width of the reflectance plate. The effective width w is the width of the entrance and exit surfaces. The height and width of the beam of light from the slit 54 are given the respective designations h and w with the appropriate location subscripts noted in FIG. 6.

The height of the internal reflectance crystal is selected so that, with the tangential image formed at its entrance end surface position 74, the distorted height $h_T$ of that image is less than the height of the plate. The width $w_T$ of the tangential image is undistorted and the crystal dimensions are selected such that the width $w_T$ and the effective width w of the crystal are approximately equal. This is shown at position 74 in FIG. 7.

Absent the internal reflectance crystal, the sagittal image would be formed at position 82 in FIG. 6. Because the beam of light diverges in width, that is in the tangential plane, after the tangential image, the sagittal image at position 82 in air would have a distorted width. On the other hand, the beam would continue to converge in height in the sagittal plane of FIG. 6 to an undistorted height at sagittal image position 82.

Due to refraction of the light entering the entrance end surface, the beam of light in the reflectance crystal converges less rapidly in the vertical plane that it would in air. Thus, the real sagittal image is formed to the right of the virtual image but has a height the same as the virtual image. The crystal and optical system are selected such that this sagittal image is formed at the exit end surface 76 of the crystal.

Because the beam of light is internally reflected by the reflecting surfaces of the internal reflectance crystal, the beam emitted from the crystal is limited to the width of the exit end surface as shown at position 76 in FIG. 7. Thus, the emitted beam has a height equal to the undistorted sagittal image height and a width equal to the undistorted tangential image width which matches the effective crystal width. Although the ratio of height to width of the emerging beam is a little different from that of the slit, the product of beam area times the solid angle of the rays is the same for the beam emerging from the ATR crystal as it is for the beam leaving the slit. Thus, the brightness of the beam at the exit face of the crystal is not diminished by beam spreading within the crystal. The image of the beam leaving the reflectance crystal is a quasiaberration-free image having an illuminated cross section and beam divergence as effective as an aberration-free image of the slit formed in air in the absence of the ATR crystal. Given an exit image of such high quality, it is a straightforward matter to efficiently transfer the energy to the detector. The net result is a significant improvement in energy transfer through the ATR crystal to the detector and a corresponding increase in the signal-to-noise radio of the spectrometer system.

The practical results of forming the astigmatic images on the respective entrance and exit end surfaces of the internal reflectance crystal can be seen in FIGS. 2 and 3 in which the illuminated region of the internal reflectance crystal is indicated by hatch marks. As shown in FIG. 2, in a vertical plane the illuminated region is at a maximum at the entrance surface and reduces to an undistorted height at the sagittal image at the exit surface. Because the beam converges in the vertical plane, light is not reflected from the upper and lower edges 42 and 44 of the crystal, and the O-ring is only illuminated near the end surfaces. On the other hand, the beam is contained in the horizontal plane by internal reflections after the tangential image at the entrance surface, so that substantially all input energy reaches the exit face.

The illumination of the entrance and exit surfaces is illustrated in FIGS. 8A and 8B. The tangential image has an undistorted width which extends across the width of the entrance surface. The distorted height extends nearly the entire height of the entrance surface. At the exit surface, the sagittal image is undistorted in height, and due to the internal reflections along the internally reflecting surface of the crystal, the width of the image at the exit surface is limited to the undistorted width of the tangential image. The sagittal image, as it would be formed in air, is shown in broken lines in FIG. 8B to illustrate the extent to which the width of the exit surface image is limited to form a quasi-aberration-free image.

With a flat exit end surface the emitted beam of light diverges in the vertical plane as shown by the broken lines 84 in FIG. 6 and in the horizontal plane as shown in FIG. 7. Thus, absent a large detector lens, a portion of the light energy would be lost to the detector. To avoid the requirement of a large detector lens which would degrade the image quality at the detector, the exit end surface of the crystal in the schematic of FIG. 6 is shown as being curved along its height in a vertical plane. The curved exit end surface, having a radius $R'$, reduces the divergence of the emitted beam and thus all of the light beam is directed toward the detector lens. $R'$ is chosen so that in the schematic of FIG. 6 the spherical mirror is imaged on the detector lens. They are both pupils (aperture stops) of the system. Due to the narrow width of the exit end surface relative to the detector lens, it is less important for the surface to be curved along its width. However, it is convenient to use a spherical convex surface on the crystal end face.

Once an internal reflectance crystal has been selected, the dimensions of the illuminating system can be calculated from several basic equations and selected parameters such as the slit dimensions. For a spherical mirror having a curvature of radius R, spaced a distance S from the source slit, and illuminated off-axis at an angle $\phi$, the tangential and sagittal images are formed at distances $S_T$ and $S_S'$ from the mirror as determined by the following two equations:

$$(1/S)+(1/S_S')=(2\cos\phi/R) \quad (1)$$

$$(1/S)+(1/S_T')=2/R\cos\phi) \quad (2)$$

Further, the magnification of the slit height at the sagittal image can be defined as:

$$M=S_S'/S=h_{sag}/h_s \quad (3)$$

and magnification of the slit width at the tangential image can be defined as:

$$M'=S_T'/S=w_T/w_S \quad (4)$$

It follows from the equations (3) and (4) that $$1/S=M/S_S'=M'/S_T' \quad (5)$$

Using equation (5), equations (1) and (2) can be rewritten as follows:

$$\frac{2\cos\phi}{R} = \frac{M}{S_S'} + \frac{1}{S_S'} \quad (6)$$

$$= \frac{1}{S_S'}(1+M) \quad (7)$$

$$\frac{2}{R\cos\phi} = \frac{M}{S_T'} + \frac{1}{S_T'} \quad (8)$$

$$= \frac{1}{S_T'}(1+M') \quad (9)$$

Equations (7) and (9) can be combined to give the following results:

$$\cos^2\phi = \frac{\frac{1}{S_S'}(1+M)}{\frac{1}{S_T'}(1+M')} \quad (10)$$

$$= \frac{M'(1+M)}{M(1+M')} \quad (11)$$

Further the distance $S_1$ along the optical axis between the tangential and virtual sagittal images should be chosen such that $$S_1=(n_1/n_2)\cdot(L/\sin\theta)=S_S'-S_T'$$

In one system, the internal reflectance crystal dimensions include $\theta=45°$, L=50 mm, t=2.17 mm and the number of reflections n=23. The crystal is of ZnSe having an index of refraction of $n_2=2.4$.

Based on initial approximations and the above equations, it can be calculated that a spherical mirror having a radius R=84 mm should be positioned at a distance S=66 mm from the slit, and offset relative to the optical axis at an angle of $\phi=17.4°$. A slit width $w_s=2$ mm and a slit height $h_s=6$ mm results in an exit beam from the crystal of 3.1 mm by 12 mm cross section. Further, if the detector lens is chosen to give a 3X demagnification of the exit beam, the beam can be detected by a 1 mm by 4 mm detector.

Without curvature of the exit end surface of the internal reflectance crystal, the height $h_e$ of the beam of light at the detector lens spaced a distance of u=40 mm from the exit end surface can be calculated from the values $S_S'=2S=132$ mm, $h_{sag}=12$ mm, and $h_m=46$ mm:

$$h_e = h_{sag} + \frac{u(h_m+h_{sag})}{S_S'} = 29.6 \text{mm}.$$

On the other hand, with a surface curvature of radius $R'=43$ mm, the height of the beam at the detector lens is as follows:

$$h_e=u\cdot h_m/S_S'=13.9 \text{ mm}.$$

Thus the field lens effect of the curved exit surface results in a much more compact beam in the vertical plane. Without this field lens effect, there would be a loss of light of vignetting of the beam at the detector lens.

The entrance end surface may also be curved to give the designer another degree of freedom in refracting the incoming beam to change the relationship between the distances $S_1$ and $L/\sin\theta$.

A possible embodiment of the invention for use as an accessory with conventional spectrometer apparatus is shown in FIG. 9. The horizontal base 86 supports the optical elements of the astigmatic illuminating system as well as means for precisely positioning an internal reflectance crystal to receive a beam of light and emit that beam of light to a light detector. The optical elements include, a spherical mirror 90 positioned on the plate 86 to receive a beam of light off-axis from the spectrometer exit slit 88, and a planar mirror 92 for reflecting the thus formed astigmatic images. The means for precisely positioning an internal reflectance crystal include a positioning plate 94 fixed to the base 86 and locating pins 96 and 98 extending upwardly from the positioning plate.

In use, an internal reflectance crystal 100 is mounted in a crystal holder 102. The crystal holder has bores therein for receiving the pins 96 and 98 and precisely positioning the holder, and thus the internal reflectance crystal, with respect to the astigmatic illuminating system. Light leaving the slit 88 illuminates the internal reflectance crystal in the manner already described with the tangential image formed at the entrance surface of crystal 100 and the sagittal image formed at the exit surface of the crystal 100. Light emitted from the thus positioned crystal is detected by a detector in the main spectrometer apparatus.

While the invention has been particularly shown and described with reference to preferred embodiments thereof, it will be understood by those skilled in the art that various changes in form and details may be made therein without departing from the spirit and scope of the invention as defined by the appended claims. For example the invention would lead to improvements in grating spectrophotometers or Fourier Transform Spectrometers.

Paradoxically, the high-quality image at the exit of the ATR crystal is achieved through a deliberate introduction of a calculated amount of astigmatism into the beam as it enters the crystal. In the embodiment described here, a spherical mirror illuminated off-axis produces the required astigmatism. Equally well, a lens with a cylindrical component or a toroidal mirror could be used to produce the astigmatism. The spherical mirror used off-axis is a method of choice here because of its simplicity. The toroid would give additional design flexibility.

The selected frequency in a spectrometer is isolated by a monochromator. Although the monochromator slit in the above-described system is positioned before the crystal, it might also be placed between the crystal and the detector.

As used in the following claims, the term "light" refers to electromagnetic radiation including, but not limited to, radiation in the infrared, visible, and ultraviolet spectra.

I claim:

1. An internal reflection spectrometer comprising:
   a light source;
   means for forming first and second astigmatic images of said light source;
   an internal reflectance crystal having a light-entrance end surface and a light-exit end surface, and two opposed internally reflecting surfaces extending between said end surfaces to multiply internally reflect light therebetween, said internal reflectance crystal being so positioned that one of said astigmatic images having a distorted height is formed at about said entrance end surface and the other of said astigmatic images having a distorted width is formed at about said exit end surface;
   means for positioning a test sample adjacent at least one of said internally reflecting surfaces; and
   means for detecting light passing through the exit end surface of said internal reflectance crystal.

2. An internal reflection spectrometer as claimed in claim 1 wherein said light source includes a beam defining slit and wherein said entrance end surface of said internal reflector plate has a width approximating the undistorted width of said first astigmatic image.

3. An internal reflection spectrometer as claimed in claim 2 wherein the distorted height of said first astigmatic image is less than the height of said entrance end surface.

4. An internal reflection spectrometer as claimed in claim 2 wherein the exit end surface of said internal reflector plate is curved throughout its height to refract said beam of light as it passes through said exit end surface and reduce the divergence of said beam of light.

5. An internal reflection spectrometer as claimed in claim 1 wherein said first image has a distorted height less than the height of said entrance end surface.

6. An internal reflection spectrometer as claimed in claim 1 wherein the exit end surface of said internal reflector plate is curved throughout its height to refract said beam of light as it passes through said exit end surface and reduce the divergence of said beam of light.

7. An internal reflection spectrometer as claimed in claim 1 wherein said image forming means comprises a spherical mirror illuminated off-axis by said beam of light.

8. An internal reflection spectrometer comprising:
   a light source emitting a beam of light along an optical axis;
   image forming means in the optical path of said beam of light for forming first and second astigmatic images of said light source, said first astigmatic image having a distorted height and said second astigmatic image having a distorted width;
   an internal reflectance crystal positioned in the optical path of said beam of light having a light-entrance end surface at about said first image and a light-exit end surface at about said second image, and two opposed internally reflecting surfaces extending between said end surfaces and positioned to internally reflect said beam of light along said optical axis, at least one of said internally reflecting surfaces having a test sample adjacent thereto;
   said internally reflecting surfaces defining the widths of said end surfaces and thus defining the maximum widths of said beam of light as said beam passes through said entrance end surface and said exit end surface;
   said internal reflectance crystal being so positioned in the optical path of said beam of light that said beam of light, when within said internal reflectance crystal, diverges in width, the width of said beam of light passing through said exit end surface being limited by the width of that surface; and
   light detecting means for detecting said beam of light passing through the exit end of said internal reflectance crystal.

9. An internal reflection spectrometer as claimed in claim 8 wherein said beam of light passes through said entrance end surface of said internal reflectance crystal before it is focused into said second astigmatic image and the height of said beam passing through said entrance end surface is less than the height of said entrance end surface.

10. A internal reflection spectrometer as claimed in claim 9 wherein said first astigmatic image is formed at said entrance end surface of said internal reflectance crystal.

11. An internal reflection spectrometer as claimed in claim 8 wherein said second astigmatic image is formed at the exit end surface of said internal reflectance crystal and the distorted width of said second image is limited by the width of said exit end surface.

12. An internal reflection spectrometer as claimed in claim 11 wherein said light source includes a slit and wherein the width of said exit end surface approximates the undistorted width of said first astigmatic image.

13. An internal reflection spectrometer as claimed in claim 12 wherein the exit end surface of said internal reflectance crystal is curved throughout its height to refract said beam of light as it passes through said exit end surface and reduce the divergence of said beam of light.

14. An internal reflection spectrometer as claimed in claim 11 wherein the exit end surface of said internal reflectance crystal is curved throughout its height to refract said beam of light as it passes through said exit end surface and reduce the divergence of said beam of light.

15. An internal reflection spectrometer as claimed in claim 8 wherein said image forming means comprises a spherical mirror illuminated off-axis by said beam of light.

16. A sample illuminating system for an internal reflection spectrometer of the type in which a beam of light is transmitted from a source of light through an internal reflectance crystal having a light-entrance end surface and a light-exit end surface and two opposed internally reflecting surfaces extending between said end surfaces, at least one of said internally reflecting surfaces having a test sample adjacent thereto, said sample illuminating system comprising:
an optical system including a spherical mirror for receiving a beam of light off-axis from a light source and for forming first and second astigmatic images of the light source, said first astigmatic image having a distorted height and said second astigmatic image having a distorted width; and
positioning means for precisely positioning said internal reflectance crystal as an element of said optical system with its light-entrance end surface at about said first image and its light-exit end surface at about said second image for receiving the beam of light off-axis from said spherical mirror and emitting that beam of light to a light detector.

17. A sample illuminating system for an internal reflection spectrometer of the type in which a beam of light is transmitted from a source of light through an internal reflectance crystal having a light-entrance end surface and light-exit end surface and two opposed internally reflecting surfaces extending between said end surfaces, at least one of said internally reflecting surfaces having a test sample adjacent thereto, said sample illuminating system comprising:
an optical system comprising forming means for receiving a beam of light from a light source and for forming first and second astigmatic images of said light source, said first astigmatic image having a distorted height and said second astigmatic image having a distorted width; and
means for precisely positioning an internal reflectance crystal as an element of said optical system to receive said beam of light and emit that beam of light to a light detector, said first astigmatic image being formed at about the entrance end surfce of the precisely positioned internal reflectance crystal and said second astigmatic image being formed at about the exit end surface of the internal reflectance crystal.

18. A method of illuminating an internal reflector plate having a light-entrance end surface, a light-exit end surface, and two opposed internally reflecting surfaces extending between said end surfaces, said method comprising the steps of:
emitting a beam of light from a light source;
focusing said beam of light with an astigmatism; and
forming a first astigmatic image of said light source, having a distorted height, at about the entrance end surface of said internal reflector plate and forming a second astigmatic image of said light source, having a distorted width, at about the exit end surface of said internal reflector plate.

19. A method of illuminating an internal reflector plate as claimed in claim 18 wherein said beam of light is focused by a spherical mirror illuminated off-axis.

* * * * *